(12) United States Patent
Chen et al.

(10) Patent No.: US 10,295,482 B1
(45) Date of Patent: May 21, 2019

(54) SPECTRUM-INSPECTION DEVICE AND METHOD FOR FORMING THE SAME

(71) Applicant: VisEra Technologies Company Limited, Hsin-Chu (TW)

(72) Inventors: Yu-Jen Chen, Taoyuan (TW); Wei-Ko Wang, Taoyuan (TW)

(73) Assignee: VISERA TECHNOLOGIES COMPANY LIMITED, Hsin-Chu (TW)

( * ) Notice: Subject to any disclaimer, the term of this patent is extended or adjusted under 35 U.S.C. 154(b) by 0 days.

(21) Appl. No.: 15/853,353

(22) Filed: Dec. 22, 2017

(51) Int. Cl.
| | |
|---|---|
| *H04N 9/077* | (2006.01) |
| *H04N 5/374* | (2011.01) |
| *H04N 9/04* | (2006.01) |
| *H04N 5/33* | (2006.01) |
| *G02B 5/20* | (2006.01) |
| *G02B 3/00* | (2006.01) |
| *G01N 23/06* | (2018.01) |
| *G01N 21/65* | (2006.01) |
| *G02B 13/14* | (2006.01) |
| *G01T 1/17* | (2006.01) |
| *G01T 1/36* | (2006.01) |

(52) U.S. Cl.
CPC ............ *G01N 23/06* (2013.01); *G01N 21/65* (2013.01); *G01T 1/17* (2013.01); *G01T 1/36* (2013.01); *G02B 3/005* (2013.01); *G02B 5/208* (2013.01); *G02B 13/14* (2013.01); *H04N 5/332* (2013.01); *H04N 5/374* (2013.01); *H04N 9/045* (2013.01); *H04N 9/077* (2013.01)

(58) Field of Classification Search
CPC ........ G01N 23/04; G01N 21/27; G01N 21/65; G01N 27/9033; G01N 23/06; G01T 7/00; G01T 1/36; G01T 3/00; G01T 1/17; G02B 5/208; G02B 5/28; G02B 13/14; G02B 3/005; H04N 5/332; H04N 5/374; H04N 9/077; H04N 9/045
USPC ....................................... 250/459.1
See application file for complete search history.

(56) References Cited

U.S. PATENT DOCUMENTS

| | | | |
|---|---|---|---|
| 2001/0043330 A1* | 11/2001 | Jung .................. | G01J 1/06 356/419 |
| 2008/0144177 A1* | 6/2008 | Miller ................ | G01J 3/02 359/489.07 |

(Continued)

*Primary Examiner* — Taeho Jo
(74) *Attorney, Agent, or Firm* — Muncy, Geissler, Olds & Lowe, P.C.

(57) ABSTRACT

A spectrum-inspection device includes a substrate including a first photodiode and a second photodiode. The spectrum-inspection device also includes an interference-type filter disposed over the first and second photodiodes. The interference-type filter allows a first light beam with wavelength of a multi-band to pass through. The multi-band includes a first waveband, a second waveband, a third waveband, and a fourth waveband. The spectrum-inspection device also includes a first absorption-type filter disposed over the first and second photodiodes. The first absorption-type filter allows a second light beam with wavelength of a first region to pass through. The spectrum-inspection device further includes a second absorption-type filter disposed over the second photodiode. The second absorption-type filter is disposed over the first absorption-type filter and allows a third light beam with wavelength of a second region to pass through, wherein the second region overlaps the first region.

16 Claims, 10 Drawing Sheets

(56) References Cited

U.S. PATENT DOCUMENTS

| | | | |
|---|---|---|---|
| 2012/0133799 A1* | 5/2012 | Findlay | G01S 7/4816 348/241 |
| 2012/0187512 A1* | 7/2012 | Wang | H01L 27/14618 257/432 |
| 2013/0300905 A1* | 11/2013 | Mabuchi | H01L 24/17 348/300 |
| 2014/0027876 A1* | 1/2014 | Holenarsipur | H01L 27/14621 257/432 |
| 2014/0034835 A1* | 2/2014 | Frey | G01J 1/0437 250/349 |
| 2014/0124797 A1* | 5/2014 | Jones | G01S 17/026 257/80 |
| 2014/0146297 A1* | 5/2014 | Vainer | G01N 21/94 355/30 |
| 2015/0090866 A1* | 4/2015 | Lee | G01S 17/88 250/226 |
| 2015/0221691 A1* | 8/2015 | Watanabe | H04N 5/332 348/164 |
| 2016/0099272 A1* | 4/2016 | Wang | H01L 27/14621 257/435 |
| 2016/0099280 A1* | 4/2016 | Huang | H01L 27/14621 250/208.1 |
| 2016/0116653 A1* | 4/2016 | Murayama | H01L 27/14618 359/359 |
| 2016/0161332 A1* | 6/2016 | Townsend | G02B 5/201 250/208.2 |
| 2016/0172399 A1* | 6/2016 | Nakata | H01L 27/14621 348/308 |
| 2017/0034456 A1* | 2/2017 | Kyung | H04N 5/332 |
| 2017/0040367 A1* | 2/2017 | Wang | H01L 27/14621 |
| 2017/0041560 A1* | 2/2017 | Gotoh | G01J 3/36 |
| 2017/0059754 A1* | 3/2017 | Frey | G01J 3/26 |
| 2017/0090083 A1* | 3/2017 | Takishita | B05D 5/06 |
| 2017/0111618 A1* | 4/2017 | Hsieh | G02B 3/005 |
| 2017/0187948 A1* | 6/2017 | Wang | G02B 3/0006 |
| 2017/0263662 A1* | 9/2017 | Hsieh | H01L 27/14621 |
| 2017/0317131 A1* | 11/2017 | Shimada | H01L 27/14 |
| 2017/0317132 A1* | 11/2017 | Hatakeyama | H01L 27/14 |
| 2017/0345860 A1* | 11/2017 | Nagaya | G02B 5/22 |
| 2017/0347086 A1* | 11/2017 | Watanabe | G06T 7/521 |
| 2018/0076253 A1* | 3/2018 | Hsieh | H01L 27/1462 |
| 2018/0076258 A1* | 3/2018 | Hsieh | H01L 27/14685 |
| 2018/0084167 A1* | 3/2018 | Qian | H04N 5/2254 |
| 2018/0088588 A1* | 3/2018 | Ion | G02B 5/201 |

* cited by examiner

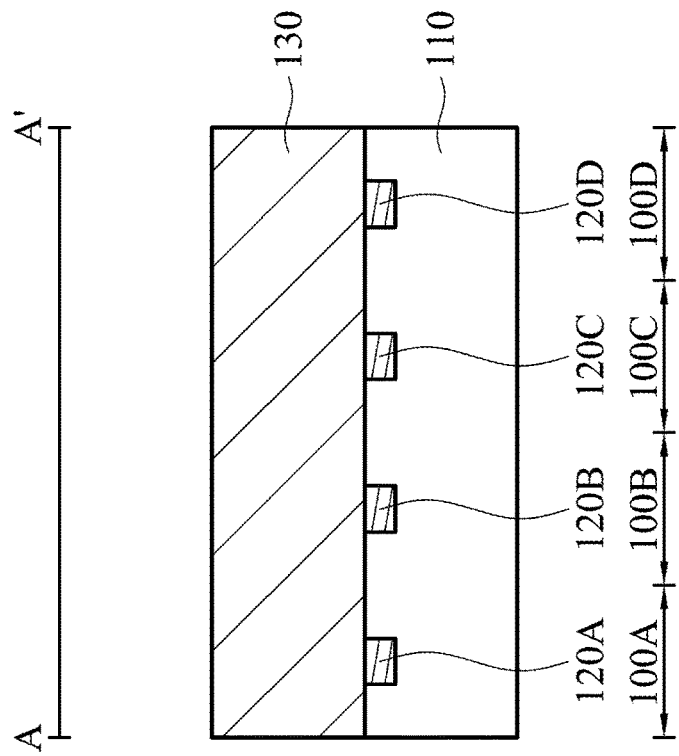
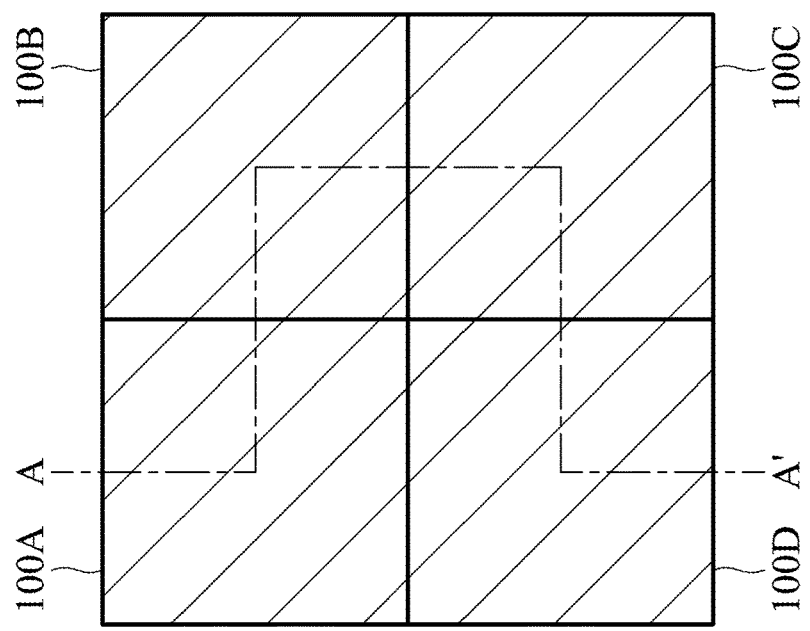
FIG. 1B
FIG. 1A

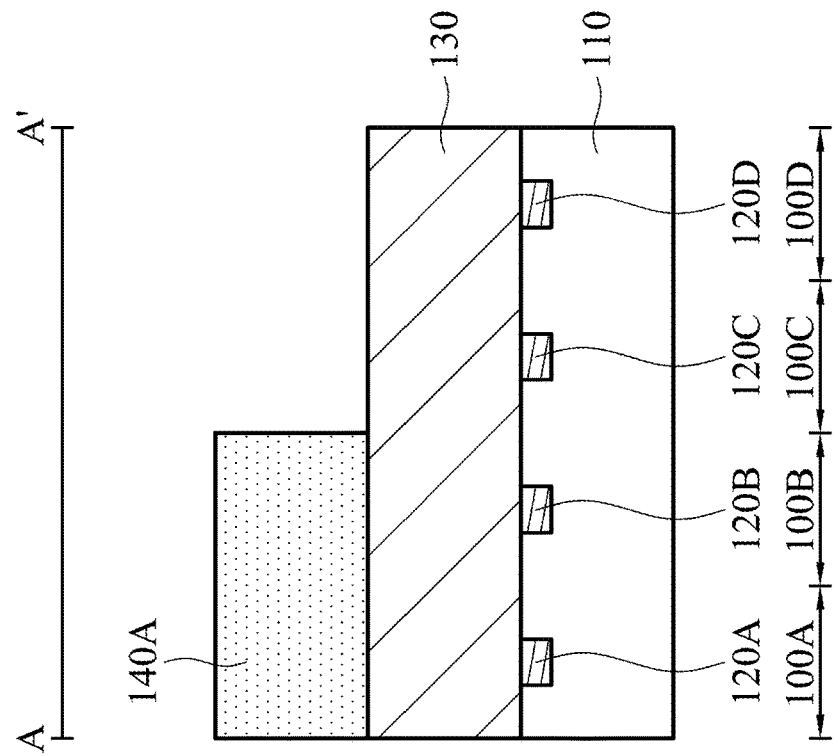
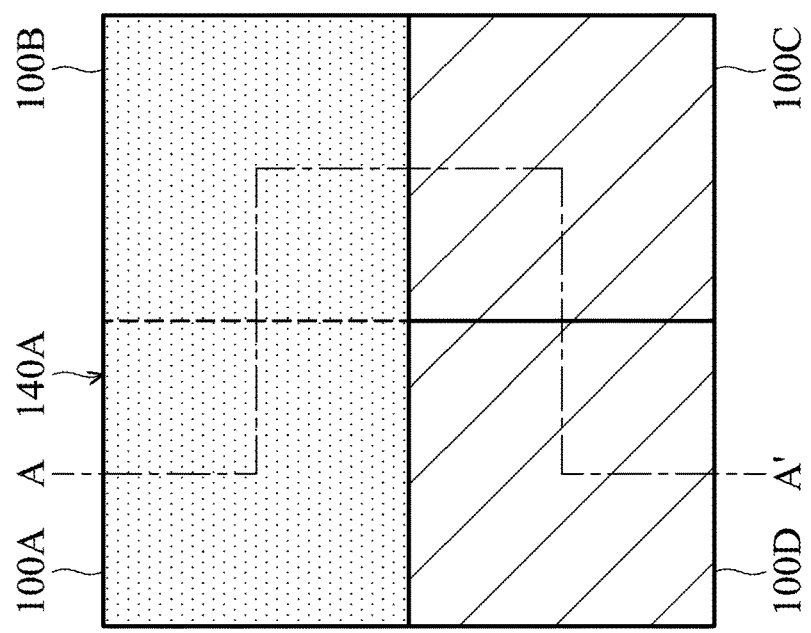
FIG. 2B
FIG. 2A

SPECTRUM-INSPECTION DEVICE AND METHOD FOR FORMING THE SAME

BACKGROUND

Field of the Invention

The present disclosure relates to a spectrum-inspection device, and in particular to a spectrum-inspection device including an absorption-type filter and an interference-type filter.

Description of the Related Art

A conventional spectrum meter is an optical system with a large number of optical elements, such as beam splitters, collimators, focusing mirrors, and linear sensors. The beam splitters may be prisms or gratings. The collimators and the focusing mirrors are configured to shorten the optical path in the optical system. Therefore, the size and weight of the conventional spectrum meter are great, and the manufacturing cost of the conventional spectrum meter is expensive.

Moreover, the linear sensor of the conventional spectrum meter is linear. The conventional spectrum meter is only used to measure a linear spectrum of a sample, and the applications of the conventional spectrum meter are restricted.

Although conventional spectrum meters have been generally adequate for their intended purposes, they have not been entirely satisfactory in all respects. Consequently, it is desirable to provide a solution for improving spectrum meters.

BRIEF SUMMARY

According to some embodiments, a spectrum-inspection device is provided. The spectrum-inspection device includes a substrate including a first photodiode and a second photodiode. The spectrum-inspection device also includes an interference-type filter disposed over the first photodiode and the second photodiode. The interference-type filter allows a first light beam with wavelength of a multi-band to pass through, and the multi-band comprises a first waveband, a second waveband, a third waveband, and a fourth waveband. The spectrum-inspection device also includes a first absorption-type filter disposed over the first photodiode and the second photodiode. The first absorption-type filter allows a second light beam with the wavelength of a first region to pass through. The spectrum-inspection device further includes a second absorption-type filter disposed over the second photodiode. The second absorption-type filter allows a third light beam with the wavelength of a second region to pass through, and wherein the second region overlaps the first region.

According to some embodiments, a method for forming a spectrum-inspection device is provided. The method includes providing a substrate which includes a first photodiode and a second photodiode. The method also includes forming an interference-type filter over the first photodiode and the second photodiode. The interference-type filter allows a first light beam with wavelength of a multi-band to pass through. The multi-band comprises a first waveband, a second waveband, a third waveband, and a fourth waveband. The method further includes forming a first absorption-type filter over the first photodiode and the second photodiode. The first absorption-type filter allows a second light beam with the wavelength of a first region to pass through. In addition, the method includes forming a second absorption-type filter over the second photodiode. The second absorption-type filter allows a third light beam with the wavelength of a second region to pass through, and wherein the second region overlaps the first region.

A detailed description is given in the following embodiments with reference to the accompanying drawings.

BRIEF DESCRIPTION OF DRAWINGS

The invention can be more fully understood by reading the subsequent detailed description and examples with references made to the accompanying drawings, wherein:

FIGS. 1A, 2A, 3A and 4A are top views for illustrating various stages of a process for forming a spectrum-inspection device, in accordance with some embodiments.

FIGS. 1B, 2B, 3B and 4B are cross-sectional views for illustrating various stages of a process for forming a spectrum-inspection device, in accordance with some embodiments.

DETAILED DESCRIPTION

Figure 3B:
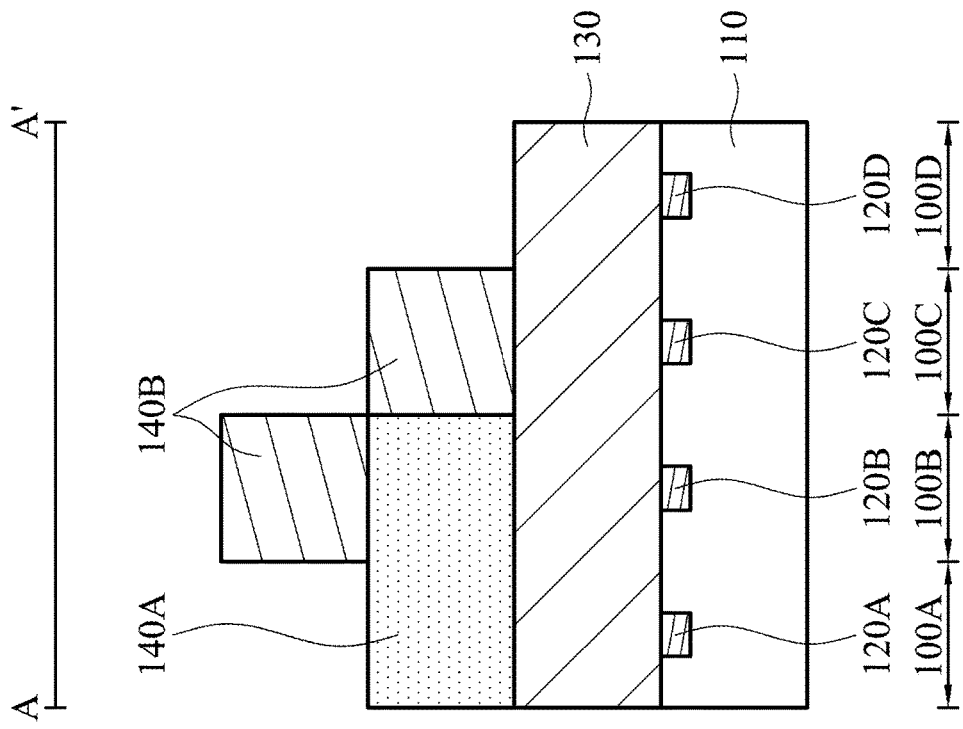

The spectrum-inspection device of the present disclosure is described in detail in the following description. In the following detailed description, for purposes of explanation, numerous specific details and embodiments are set forth in order to provide a thorough understanding of the present disclosure. The specific elements and configurations described in the following detailed description are set forth in order to clearly describe the present disclosure. It will be apparent, however, that the exemplary embodiments set forth herein are used merely for the purpose of illustration, and the inventive concept may be embodied in various forms without being limited to those exemplary embodiments. In addition, the drawings of different embodiments may use like and/or corresponding numerals to denote like and/or corresponding elements in order to clearly describe the present disclosure. However, the use of like and/or corresponding numerals in the drawings of different embodiments does not suggest any correlation between different embodiments. In addition, in this specification, expressions such as "first material layer disposed on/over a second material layer", may indicate the direct contact of the first material layer and the second material layer, or it may indicate a non-contact state with one or more intermediate layers between the first material layer and the second material layer. In the above situation, the first material layer may not be in direct contact with the second material layer.

It should be noted that the elements or devices in the drawings of the present disclosure may be present in any form or configuration known to those skilled in the art. In addition, the expression "a layer overlying another layer", "a layer is disposed above another layer", "a layer is disposed on another layer" and "a layer is disposed over another layer" may indicate that the layer is in direct contact with the other layer, or that the layer is not in direct contact with the other layer, there being one or more intermediate layers disposed between the layer and the other layer.

In addition, in this specification, relative expressions are used. For example, "lower", "bottom", "higher" or "top" are used to describe the position of one element relative to another. It should be appreciated that if a device is flipped upside down, an element that is "lower" will become an element that is "higher".

The terms "about" and "substantially" typically mean+/−20% of the stated value, more typically +/−10% of the stated value, more typically +/−5% of the stated value, more typically +/−3% of the stated value, more typically +/−2% of the stated value, more typically +/−1% of the stated value and even more typically +/−0.5% of the stated value. The stated value of the present disclosure is an approximate value. When there is no specific description, the stated value includes the meaning of "about" or "substantially".

It should be understood that, although the terms first, second, third etc. may be used herein to describe various elements, components, regions, layers, portions and/or sections, these elements, components, regions, layers, portions and/or sections should not be limited by these terms. These terms are only used to distinguish one element, component, region, layer, portion or section from another region, layer or section. Thus, a first element, component, region, layer, portion or section discussed below could be termed a second element, component, region, layer, portion or section without departing from the teachings of the present disclosure.

Unless defined otherwise, all technical and scientific terms used herein have the same meaning as commonly understood by one of ordinary skill in the art to which this disclosure belongs. It should be appreciated that, in each case, the term, which is defined in a commonly used dictionary, should be interpreted as having a meaning that conforms to the relative skills of the present disclosure and the background or the context of the present disclosure, and should not be interpreted in an idealized or overly formal manner unless so defined.

This description of the exemplary embodiments is intended to be read in connection with the accompanying drawings, which are to be considered part of the entire written description. The drawings are not drawn to scale. In addition, structures and devices are shown schematically in order to simplify the drawing.

In the description, relative terms such as "lower," "upper," "horizontal," "vertical,", "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

Referring to FIGS. 1A-4A and 1B-4B, a process for forming a spectrum-inspection device 100, in accordance with some embodiments is shown, wherein FIGS. 1A-4A are top views, and FIGS. 1B-4B are cross-sectional views along line A-A' of top views shown in FIGS. 1A-4A.

As shown in FIGS. 1A and 1B, the spectrum-inspection device 100 includes a substrate 110. The substrate 110 has four pixels such as a first pixel 100A with a first photodiode 120A, a second pixel 100B with a second photodiode 120B, a third pixel 100C with a third photodiode 120C and a fourth pixel 100D with a fourth photodiode 120D. In some embodiments, the first pixel 100A, the second pixel 100B, the third pixel 100C and the fourth pixel 100D form a two-dimensional pixel array.

In some embodiments, the spectrum-inspection device 100 is an image sensor, such as a CMOS (Complementary Metal-Oxide-Semiconductor) sensor, a FSI (Frontside illumination) or BSI (backside illumination) CMOS sensor, or another suitable sensor.

The substrate 110 may include, but is not limited to, a semiconductor substrate such as a silicon substrate. In addition, the substrate 110 may include an element semiconductor which may include germanium; a compound semiconductor which may include silicon carbide, gallium arsenide, gallium phosphide, indium phosphide, indium arsenide and/or indium antimonide; an alloy semiconductor which may include SiGe alloy, GaAsP alloy, AlInAs alloy, AlGaAs alloy, GaInAs alloy, GaInP alloy and/or GaInAsP alloy, or a combination thereof. In addition, the substrate 110 may include a semiconductor-on-insulator (SOI).

The first photodiode 120A, the second photodiode 120B, the third photodiode 120C and the fourth photodiode 120D are formed in the first pixel 100A, the second pixel 100B, the third pixel 100C and the fourth pixel 100D of the substrate 110, respectively. The photodiodes may include a p-n junction structure or a PIN (p-type, intrinsic and n-type) structure. The current is generated when photons are absorbed in the photodiodes, and a light signal is converted into a current signal. It should be noted that the structures shown in FIGS. 1B-4B are merely examples for better understanding the concept of the disclosure, and the scope of disclosure is not intended to be limiting. That is, besides the photodiode, the substrate 110 may include more semiconductor elements in various embodiments.

Figure 5:
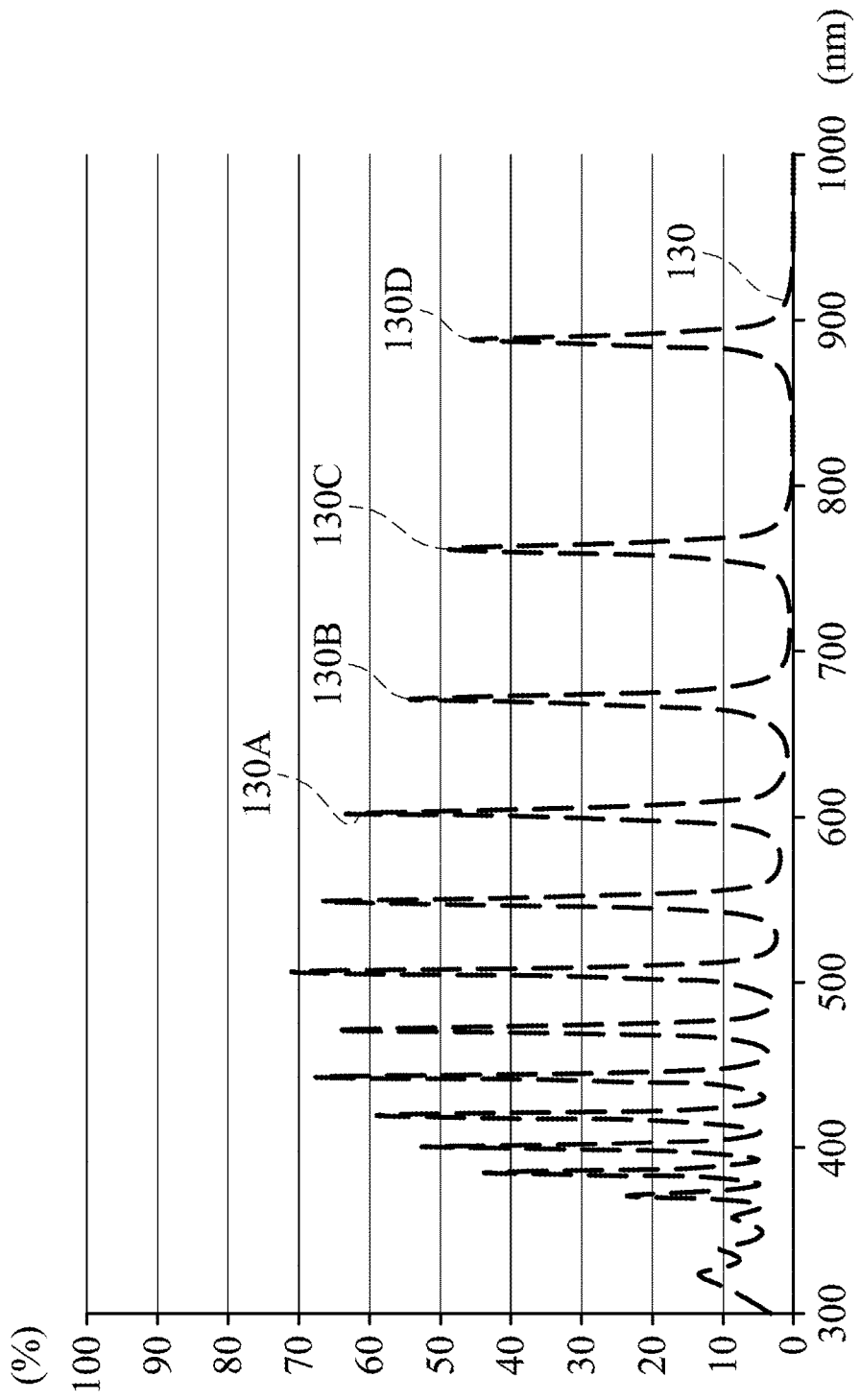
FIG. 5 is a graph of transmittance against wavelength to illustrate the optical characteristics of the interference-type filter according to some embodiments.

In some embodiments, the spectrum-inspection device 100 includes an interference-type filter 130 disposed over the first pixel 100A, the second pixel 100B, the third pixel 100C and the fourth pixel 100D of the substrate 110. In some embodiments, the interference-type filter 130 is an interference-type filter, and may be formed by a deposition process. The deposition process includes, but is not limited to, physical vapor deposition (PVD), chemical vapor deposition (CVD), sputtering, resistive thermal evaporation, electron beam evaporation, and any other applicable methods. Referring to FIG. 5, FIG. 5 is a graph of transmittance against wavelength to illustrate the optical characteristics of the interference-type filter 130 according to some embodiments. As shown in FIG. 5, the interference-type filter 130 allows a light beam with wavelength of a multi-band to pass through. In some embodiments, every band is a narrow band, and ranges between about 380 nm and about 900 nm. In some embodiments, the multi-band includes a first waveband 130A, a second waveband 130B, a third waveband 130C and a fourth waveband 130D, and these wavebands range between about 580 nm and about 900 nm.

Figure 6:
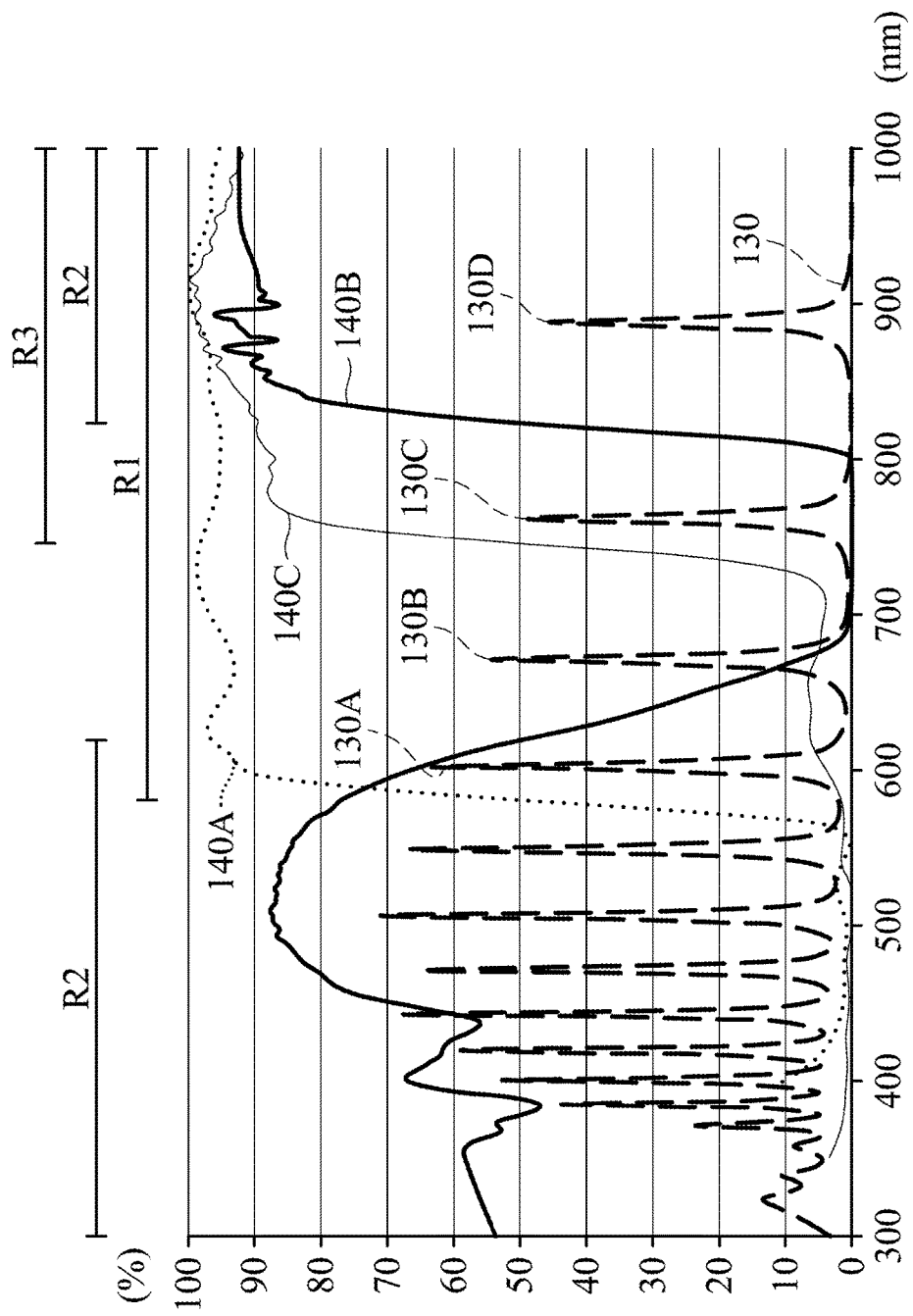
FIG. 6 is a graph of transmittance against wavelength to illustrate the optical characteristics of the absorption-type filter and the interference-type filter, according to some embodiments.

Referring to FIG. 2A and FIG. 2B, a first absorption-type filter 140A is deposited over the interference-type filter 130. In some embodiments, the first absorption-type filter 140A is deposited over the first pixel 100A and the second pixel 100B of the substrate 110. Referring to FIG. 6, FIG. 6 shows a graph of transmittance against wavelength to illustrate the optical characteristics of the first absorption-type filter 140A, according to some embodiments. As shown in FIG. 6, the first absorption-type filter 140A allows the light beam of the wavelength of first region R1 to pass through. In some embodiments, the first region R1 is higher than about 580 nm, and includes the first waveband 130A, the second waveband 130B, the third waveband 130C and the fourth waveband 130D.

Figure 3A:
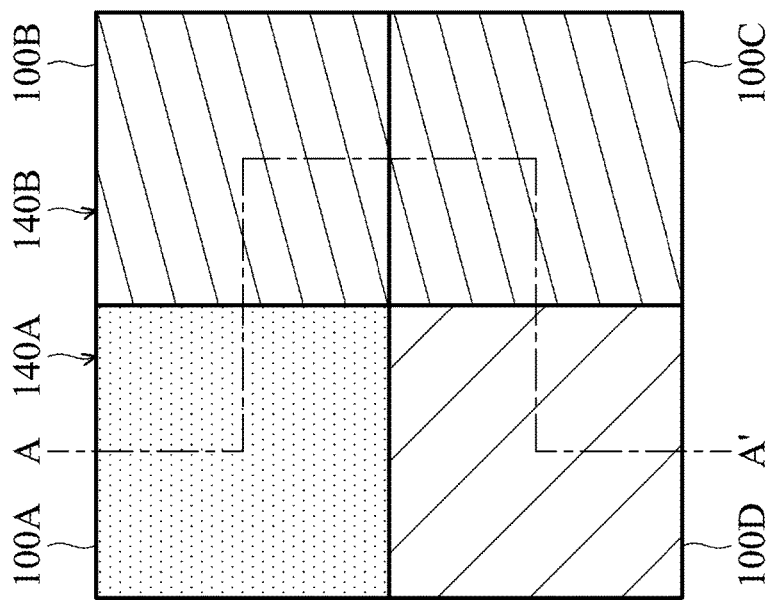

Referring to FIG. 3A and FIG. 3B, after the first absorption-type filter 140A is formed over the interference-type filter 130, a second absorption-type filter 140B is deposited over the interference-type filter 130. In some embodiments, the second absorption-type filter 140B is deposited over the second pixel 100B and the third pixel 100C of the substrate 110. As shown in FIG. 3B, the second absorption-type filter 140B over the second pixel 100B is formed above the first absorption-type filter 140A over the second pixel 100B, and the second absorption-type filter 140B over the third pixel 100C and the first absorption-type filter 140A over the second pixel 100B are in the same horizontal layer. Referring to FIG. 6, FIG. 6 shows a graph of transmittance against wavelength to illustrate the optical characteristics of the second absorption-type filter 140B, according to some embodiments. As shown in FIG. 6, the second absorption-type filter 140B allows the light beam of the wavelength of second region R2 to pass through. In some embodiments, the second region R2 is smaller than about 650 nm and higher than about 800 nm. In some embodiments, the second region R2 includes the first waveband 130A and the fourth waveband 130D.

Figure 4B:
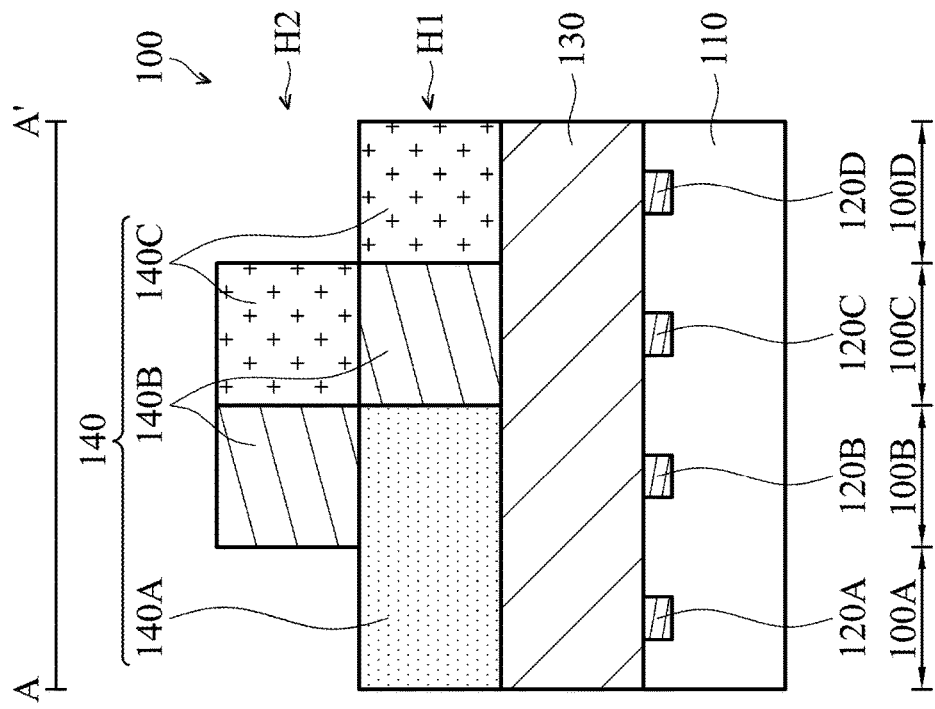
Figure 4A:
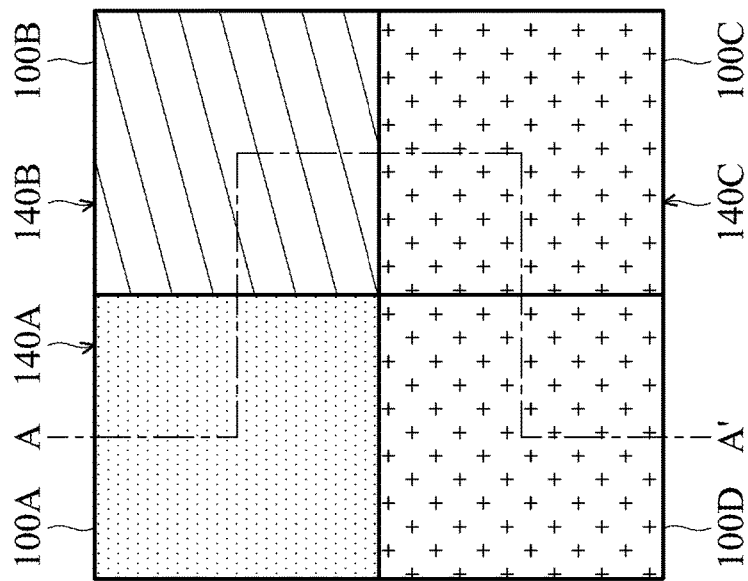

Referring to FIG. 4A and FIG. 4B, after the second absorption-type filter 140B is formed over the interference-type filter 130, a third absorption-type filter 140C is deposited over the interference-type filter 130. In some embodiments, the third absorption-type filter 140C is deposited over the third pixel 100C and the fourth pixel 100D of the substrate 110. As shown in FIG. 4B, the third absorption-type filter 140C over the third pixel 100C is formed above the second absorption-type filter 140B over the third pixel 100C. The third absorption-type filter 140C over the third pixel 100C and the second absorption-type filter 140B over the second pixel 100B are in the same horizontal layer. The third absorption-type filter 140C over the fourth pixel 100D and the second absorption-type filter 140B over the third pixel 100C are in the same horizontal layer. Referring to FIG. 6, FIG. 6 shows a graph of transmittance against wavelength to illustrate the optical characteristics of the third absorption-type filter 140C, according to some embodiments. As shown in FIG. 6, the third absorption-type filter 140C allows the light beam of the wavelength of third region R3 to pass through. In some embodiments, the third region R3 is higher than about 730 nm. The third region R3 includes the third waveband 130C and the fourth waveband 130D.

As shown in FIG. 4B, the spectrum-inspection device 100 includes interference-type filter 130 and an absorption-type filter structure 140 consisting of three filter films such as the first absorption-type filter 140A, the second absorption-type filter 140B and the third absorption-type filter 140C. In some embodiments, the absorption-type filter structure 140 includes a first horizontal layer H1 and a second horizontal layer H2. The first horizontal layer H1 includes the first absorption-type filter 140A, the second absorption-type filter 140B and the third absorption-type filter 140C. The second horizontal layer H2 includes the second absorption-type filter 140B and the third absorption-type filter 140C. In some embodiments, the absorption-type filter structure 140 includes photoresist films. In other embodiments, the absorption-type filter structure 140 may be a pigment filter made of organic films.

Figure 7A:
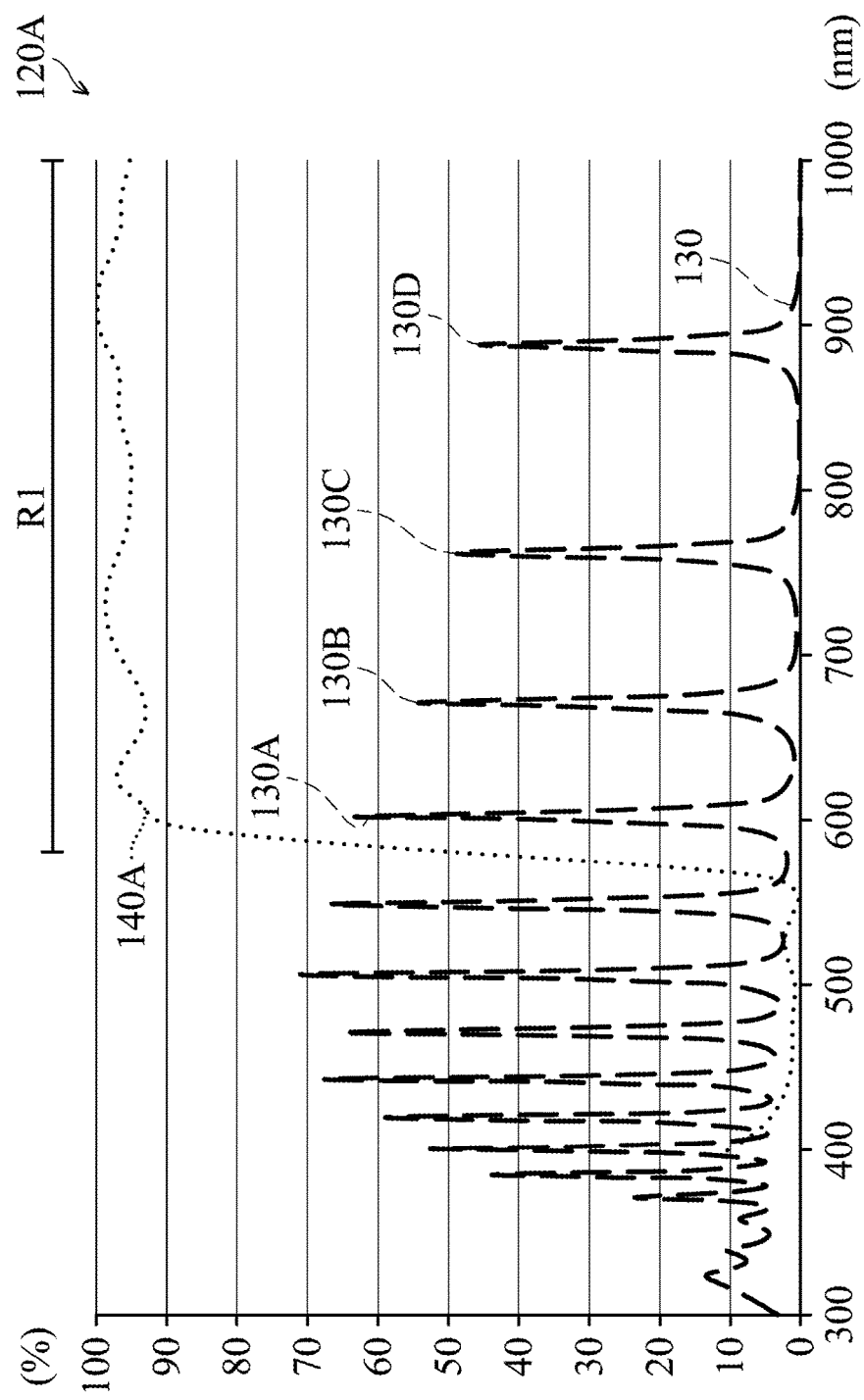
FIGS. 7A-7D are graphs of transmittance against wavelength to illustrate the wavebands received by a first photodiode, a second photodiode, a third photodiode and a fourth photodiode respectively, according to some embodiments.

As shown in FIG. 4B, the interference-type filter 130 and the first absorption-type filter 140A are formed over the first photodiode 120A of the substrate 110. Referring to FIG. 7A, FIG. 7A is a graph of transmittance against wavelength to illustrate wavebands received by the first photodiode 120A according to some embodiments. As shown in FIG. 7A, the first photodiode 120A receives the wavebands consisting of an overlapping wavelength between the multi-band and the first region R1. In this embodiment, the wavebands received by the first photodiode 120A include the first waveband 130A, the second waveband 130B, the third waveband 130C and the fourth waveband 130D.

Figure 7B:
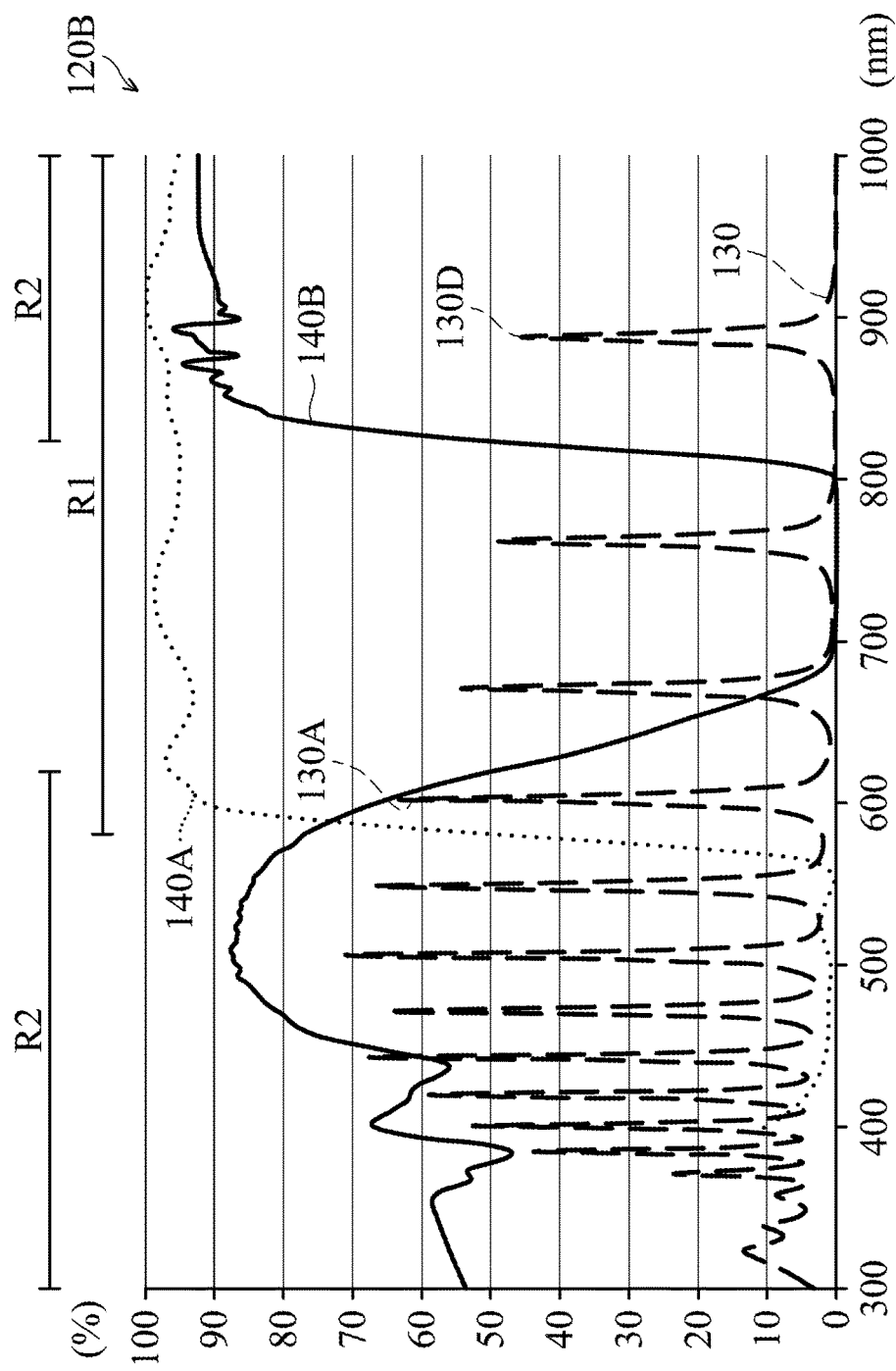

As shown in FIG. 4B, the interference-type filter 130, the first absorption-type filter 140A and the second absorption-type filter 140B are formed over the second photodiode 120B of the substrate 110. Referring to FIG. 7B, FIG. 7B is a graph of transmittance against wavelength to illustrate wavebands received by the second photodiode 120B according to some embodiments. As shown in FIG. 7B, the second photodiode 120B receives the wavebands consisting of an overlapping wavelength between the multi-band, the first region R1 and the second region R2. In this embodiment, the wavebands received by the second photodiode 120B include the first waveband 130A and the fourth waveband 130D.

Figure 7C:
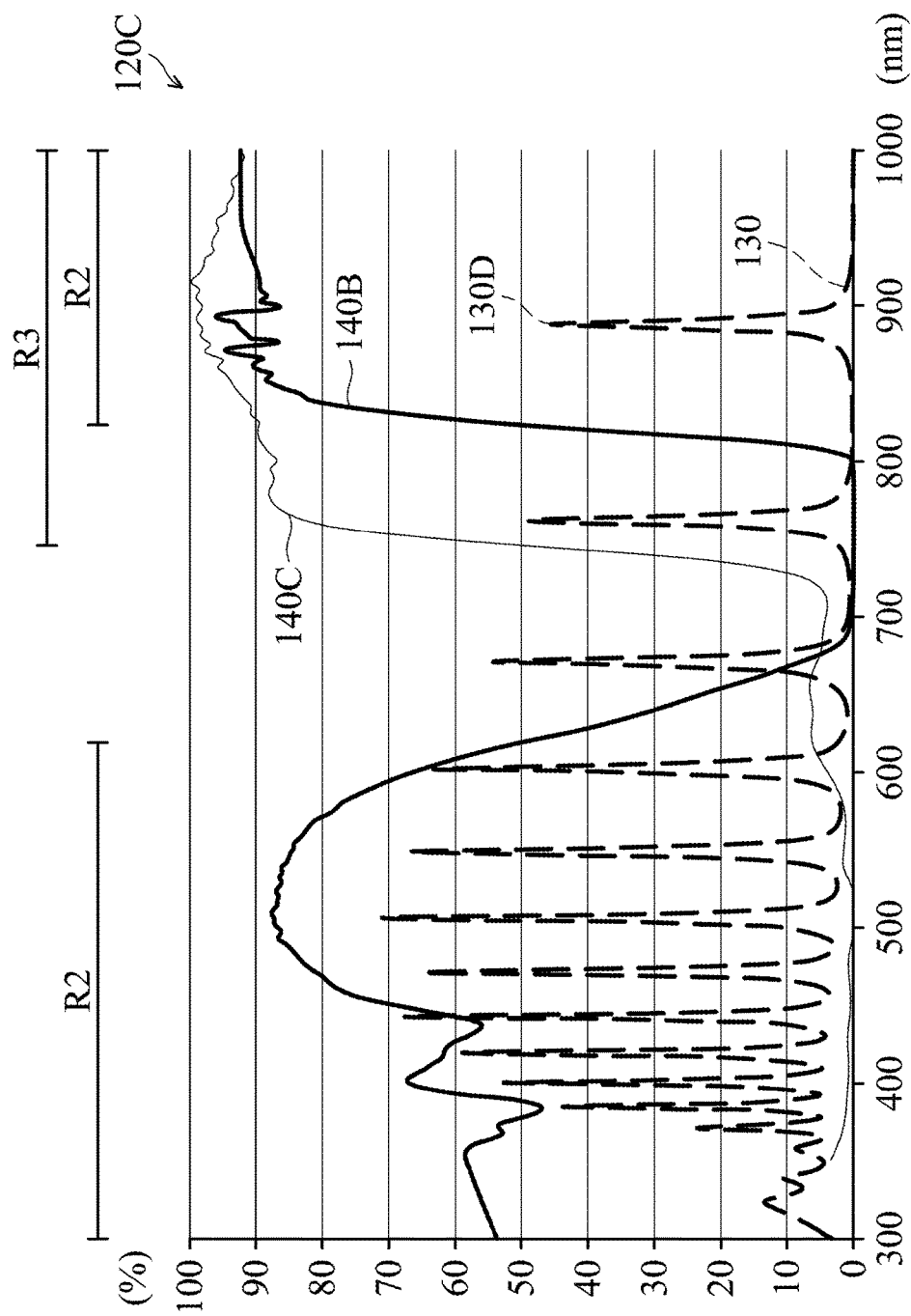

As shown in FIG. 4B, the interference-type filter 130, the second absorption-type filter 140B and the third absorption-type filter 140C are formed over the third photodiode 120C of the substrate 110. Referring to FIG. 7C, FIG. 7C is a graph of transmittance against wavelength to illustrate wavebands received by the third photodiode 120C according to some embodiments. As shown in FIG. 7C, the third photodiode 120C receives the wavebands consisting of an overlapping wavelength between the multi-band, the second region R2 and the third region R3. In this embodiment, the wavebands received by the third photodiode 120C at least include the fourth waveband 130D.

Figure 7D:
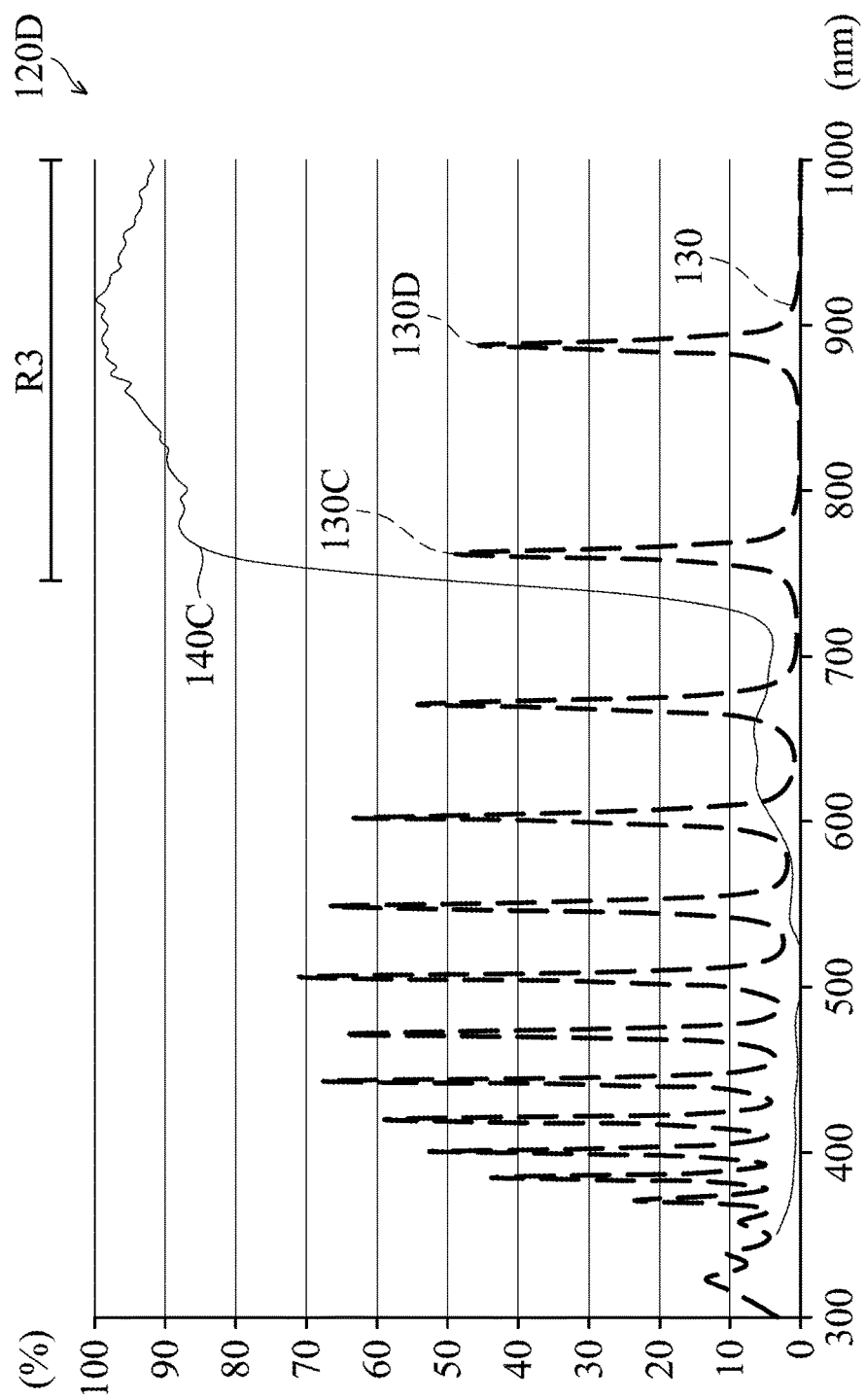

As shown in FIG. 4B, the interference-type filter 130 and the third absorption-type filter 140C are formed over the fourth photodiode 120D of the substrate 110. Referring to FIG. 7D, FIG. 7D is a graph of transmittance against wavelength to illustrate wavebands received by the fourth photodiode 120D according to some embodiments. As shown in FIG. 7D, the fourth photodiode 120D receives the wavebands consisting of an overlapping wavelength between the multi-band and the third region R3. In this embodiment, the wavebands received by the fourth photodiode 120D include the third waveband 130C and fourth waveband 130D.

In this embodiment, the first waveband 130A, the second waveband 130B, the third waveband 130C and the fourth waveband 130D are extracted independently by the algorithm. For example, the first waveband 130A, the second waveband 130B, the third waveband 130C and the fourth waveband 130D are extracted independently by as addition and/or subtraction of the wavebands received by the first photodiode 120A, the second photodiode 120B, the third photodiode 120C and the fourth photodiode 120D. For example, the third waveband 130C is determined from the third photodiode 120C and the fourth photodiode 120D by subtracting the fourth waveband 130D of the third photodiode 120C from the third waveband 130C and the fourth waveband 130D of the fourth photodiode 120D;

the first waveband 130A is determined from the second photodiode 120B and the third photodiode 120C by subtracting the fourth waveband 130D of the third photodiode 120C from the first waveband 130A and the fourth waveband 130D of the second photodiode 120B;

the second waveband 130B is determined from the first photodiode 120A, the second photodiode 120B, the third photodiode 120C and the fourth photodiode 120D by subtracting the first waveband 130A, the third waveband 130C and the fourth waveband 130D, determined from the second photodiode 120B, the third photodiode 120C and the fourth photodiode 120D, from the first waveband 130A, the second waveband 130B, the third waveband 130C and the fourth waveband 130D of the first photodiode 120A.

In this embodiment, four wavebands are extracted independently by three filter films. These three filter films may be formed by three coating processes. Since the steps of the formation for the spectrum-inspection device is simplified, the cost is reduced.

In other embodiments, the first absorption-type filter 140A, the second absorption-type filter 140B and the third absorption-type filter 140C may be selected to include different wavebands. For example, the first region R1 includes the first waveband 130A and the fourth waveband 130D, the second region R2 includes the third waveband 130C and the fourth waveband 130D, and the third region R3 includes the first waveband 130A, the second waveband 130B and the third waveband 130C. In this embodiment, the wavebands received by the first photodiode 120A include the first waveband 130A and the fourth waveband 130D, the wavebands received by the second photodiode 120B include the fourth waveband 130D, the wavebands received by the third photodiode 120C include the third waveband 130C, and the wavebands received by the fourth photodiode 120D include the first waveband 130A, the second waveband 130B and the third waveband 130C. The first waveband 130A, the second waveband 130B, the third waveband 130C and the fourth waveband 130D are extracted independently by the algorithm represented as follows:

the first waveband 130A is determined from the first photodiode 120A and the second photodiode 120B by subtracting the fourth waveband 130D of the second photodiode 120B from the first waveband 130A and the fourth waveband 130D of the first photodiode 120A; the second waveband 130B is determined from the first photodiode 120A, the second photodiode 120B, the third photodiode 120C, and the fourth photodiode 120D by subtracting the first waveband 130A and the third waveband 130C, determined from the first photodiode 120A, the second photodiode 120B and the third photodiode 120C, from the first waveband 130A, the second waveband 130B and the third waveband 130C of the fourth photodiode 120D.

In some embodiments, the first region R1 and the second region R2 at least have an overlapping wavelength, the second region R2 and the third region R3 at least have an overlapping wavelength, and the first region R1 and the third region R3 at least have an overlapping wavelength.

In some embodiments, the first region R1, the second region R2 and the third region R3 at least include two or more wavebands of the first waveband 130A, the second waveband 130B, the third waveband 130C and the fourth waveband 130D, respectively.

In addition, the method to extract different wavebands independently mentioned above may be used in N×N array, and it only need $N^2-1$ filter films to extract $N^2$ wavebands. Moreover, the method mentioned above may be used in M×N array, and it only need M×N−1 filter films to extract M×N wavebands.

In some embodiments, the interference-type filter 130 is formed over the absorption-type filter structure 140. Further, the spectrum-inspection device 100 may include more elements, but is not limited to, microlens, glass layer, Fresnel zone plate (FZP).

In some embodiments, the methods for extracting N wavebands independently include following steps: (S1) forming an interference-type filter over a substrate to allow a light beam with wavelength of a multi-band to pass through. For example, as shown in FIG. 1A, forming the interference-type filter 130 over the substrate 110. (S2) forming an absorption-type filter consisting of N−1 filter films above or under the interference-type filter, and grouping variety pixelated photodiodes as a set. For example, as shown in FIGS. 2A-4A, forming the first absorption-type filter 140A, the second absorption-type filter 140B and the third absorption-type filter 140C over the interference-type filter 130. Further, grouping the first photodiode 120A and the second photodiode 120B, grouping the second photodiode 120B and the third photodiode 120C, and grouping the third photodiode 120C and the fourth photodiode 120D as a set, respectively. (S3) overlapping the spectra of the absorption-type filter and the interference-type filter to decide N wavebands received from N photodiodes. For example, as shown in FIGS. 7A-7D, overlapping the spectra of the interference-type filter 130 and the absorption-type filter structure 140 to decide the wavebands received by the first photodiode 120A, the second photodiode 120B, the third photodiode 120C and the fourth photodiode 120D, respectively. (S4) Using algorithm such as addition and/or subtraction to extract N wavebands independently. For example, extracting the first waveband 130A, the second waveband 130B, the third waveband 130C and the fourth waveband 130D by the wavebands received by the first photodiode 120A, the second photodiode 120B, the third photodiode 120C and the fourth photodiode 120D.

Although some embodiments of the present disclosure and their advantages have been described in detail, it should be understood that various changes, substitutions and alterations can be made herein without departing from the spirit and scope of the disclosure as defined by the appended claims. For example, it will be readily understood by those skilled in the art that many of the features, functions, processes, and materials described herein may be varied while remaining within the scope of the present disclosure. Moreover, the scope of the present application is not intended to be limited to the particular embodiments of the process, machine, manufacture, composition of matter, means, methods and steps described in the specification. As one of ordinary skill in the art will readily appreciate from the disclosure of the present disclosure, processes, machines, manufacture, compositions of matter, means, methods, or steps, presently existing or later to be developed, that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:
1. A spectrum-inspection device, comprising:
   a substrate including a first photodiode, a second photodiode and a third photodiode;
   an interference-type filter disposed over the first photodiode and the second photodiode, wherein the interference-type filter allows a first light beam with wavelength of a multi-band to pass through, wherein the multi-band comprises a first waveband (a), a second waveband (b), a third waveband (c), and a fourth waveband (d);
a first absorption-type filter disposed over the first photodiode and the second photodiode, wherein the first absorption-type filter allows a second light beam with wavelength of a first region to pass through;
a second absorption-type filter disposed over the second photodiode and the third photodiode, wherein the second absorption-type filter is disposed over the first absorption-type filter, and the second absorption-type filter allows a third light beam with wavelength of a second region to pass through, and wherein the second region overlaps the first region; and
a third absorption-type filter disposed over the third photodiode, wherein the third absorption-type filter is disposed over the second absorption-type filter, and wherein the third absorption-type filter allows a fourth light beam with wavelength of a third region to pass through, and the third region overlaps at least one of the first region and the second region.

2. The spectrum-inspection device as claimed in claim 1, wherein a top surface of the third absorption-type filter disposed over the third photodiode is level with a top surface of the second absorption-type filter disposed over the second photodiode, and a top surface of the second absorption-type filter disposed over the third photodiode is level with a top surface of the first absorption-type filter disposed over the second photodiode.

3. The spectrum-inspection device as claimed in claim 1, wherein the substrate further includes a fourth photodiode, and the third absorption-type filter is further disposed over the fourth photodiode.

4. The spectrum-inspection device as claimed in claim 3, wherein the first region contains the first waveband (a), the second waveband (b), the third waveband (c) and the fourth waveband (d), the second region contains the first waveband (a) and the fourth waveband (d), and the third region contains the third waveband (c) and the fourth waveband (d), such that
the first photodiode receives the first waveband (a), the second waveband (b), the third waveband (c) and the fourth waveband (d),
the second photodiode receives the first waveband (a) and the fourth waveband (d),
the third photodiode receives the fourth waveband (d), and
the fourth photodiode receives the third waveband (c) and the fourth waveband (d).

5. The spectrum-inspection device as claimed in claim 4, wherein the third waveband (c) is determined from the third photodiode and the fourth photodiode by subtracting the fourth waveband (d) of the third photodiode from the third waveband (c) and the fourth waveband (d) of the fourth photodiode.

6. The spectrum-inspection device as claimed in claim 5, wherein the first waveband (a) is determined from the second photodiode and the third photodiode by subtracting the fourth waveband (d) of the third photodiode from the first waveband (a) and the fourth waveband (d) of the second photodiode.

7. The spectrum-inspection device as claimed in claim 6, wherein the second waveband (b) is determined from the first photodiode, the second photodiode, the third photodiode and the fourth photodiode by subtracting the first waveband (a), the third waveband (c) and the fourth waveband (d) which are determined from the second photodiode, the third photodiode and the fourth photodiode from the first waveband (a), the second waveband (b), the third waveband (c) and the fourth waveband (d) of the first photodiode.

8. The spectrum-inspection device as claimed in claim 3, wherein the first region contains the first waveband (a) and the fourth waveband (d), the second region contains the third waveband (c) and the fourth waveband (d), and the third region contains the first waveband (a), the second waveband (b), and the third waveband (c), such that
the first photodiode receives the first waveband (a) and the fourth waveband (d),
the second photodiode receives the fourth waveband (d),
the third photodiode receives the third waveband (c), and
the fourth photodiode receives the first waveband (a), the second waveband (b), and the third waveband (c).

9. The spectrum-inspection device as claimed in claim 8, wherein the first waveband (a) is determined from the first photodiode and the second photodiode by subtracting the fourth waveband (d) of the second photodiode from the first waveband (a) and the fourth waveband (d) of the first photodiode.

10. The spectrum-inspection device as claimed in claim 9, wherein the second waveband (b) is determined from the first photodiode, the second photodiode, the third photodiode, and the fourth photodiode by subtracting the first waveband (a) and the third waveband (c) which are determined from the first photodiode, the second photodiode and the third photodiode from the first waveband (a), the second waveband (b) and the third waveband (c) of the fourth photodiode.

11. A method for manufacturing a spectrum-inspection device, comprising:
providing a substrate which includes a first photodiode, a second photodiode and a third photodiode;
forming an interference-type filter over the first photodiode and the second photodiode, wherein the interference-type filter allows a first light beam with wavelength of a multi-band to pass through, and wherein the multi-band comprises a first waveband (a), a second waveband (b), a third waveband (c), and a fourth waveband (d);
forming a first absorption-type filter over the first photodiode and the second photodiode, wherein the first absorption-type filter allows a second light beam with wavelength of a first region to pass through;
forming a second absorption-type filter over the second photodiode and the third photodiode, wherein the second absorption-type filter is formed over the first absorption-type filter, and the second absorption-type filter allows a third light beam with wavelength of a second region to pass through, and wherein the second region overlaps the first region; and
forming a third absorption-type filter over the third photodiode, wherein the third absorption-type filter is further formed over the second absorption-type filter, and the third absorption-type filter allows a fourth light beam with wavelength of a third region to pass through, and wherein the third region overlaps at least one of the first region and the second region.

12. The method as claimed in claim 11, wherein the substrate further includes a fourth photodiode, and the third absorption-type filter is further formed over the fourth photodiode.

13. The method as claimed in claim 12, wherein the first region contains the first waveband (a), the second waveband (b), the third waveband (c) and the fourth waveband (d), the second region contains the first waveband (a) and the fourth waveband (d), and the third region contains the third waveband (c) and the fourth waveband (d), such that the first photodiode receives the first waveband (a), the second waveband (b), the third waveband (c) and the fourth waveband (d), the second photodiode receives the first waveband (a) and the fourth waveband (d), the third photodiode receives the fourth waveband (d), and the fourth photodiode receives the third waveband (c) and the fourth waveband (d).

14. The method as claimed in claim 13, wherein the third waveband (c) is determined from the third photodiode and the fourth photodiode by subtracting the fourth waveband (d) of the third photodiode from the third waveband (c) and the fourth waveband (d) of the fourth photodiode;

the first waveband (a) is determined from the second photodiode and the third photodiode by subtracting the fourth waveband (d) of the third photodiode from the first waveband (a) and the fourth waveband (d) of the second photodiode; and the second waveband (b) is determined from the first photodiode, the second photodiode, the third photodiode and the fourth photodiode by subtracting the first waveband (a), the third waveband (c) and the fourth waveband (d) which are determined from the second photodiode, the third photodiode and the fourth photodiode from the first waveband (a), the second waveband (b), the third waveband (c) and the fourth waveband (d) of the first photodiode.

15. The method as claimed in claim 12, wherein the first region contains the first waveband (a) and the fourth waveband (d), the second region contains the third waveband (c) and the fourth waveband (d), and the third region contains the first waveband (a), the second waveband (b), and the third waveband (c), such that the first photodiode receives the first waveband (a) and the fourth waveband (d), the second photodiode receives the fourth waveband (d), the third photodiode receives the third waveband (c), and the fourth photodiode receives the first waveband (a), the second waveband (b), and the third waveband (c).

16. The method as claimed in claim 15, wherein the first waveband (a) is determined from the first photodiode and the second photodiode by subtracting the fourth waveband (d) of the second photodiode from the first waveband (a) and the fourth waveband (d) of the first photodiode; and the second waveband (b) is determined from the first photodiode, the second photodiode, the third photodiode, and the fourth photodiode by subtracting the first waveband (a) and the third waveband (c) which are determined from the first photodiode, the second photodiode and the third photodiode from the first waveband (a), the second waveband (b) and the third waveband (c) of the fourth photodiode.

* * * * *